(12) United States Patent
Gunaratnam et al.

(10) Patent No.: US 6,796,308 B2
(45) Date of Patent: *Sep. 28, 2004

(54) MASK CUSHION AND FRAME ASSEMBLY

(75) Inventors: Michael K. Gunaratnam, Marsfield (AU); Gregory S. Smart, Randwick (AU); Philip R. Kwok, Chatswood (AU)

(73) Assignee: ResMed Limited, North Ryde (AU)

( * ) Notice: Subject to any disclaimer, the term of this patent is extended or adjusted under 35 U.S.C. 154(b) by 16 days.

This patent is subject to a terminal disclaimer.

(21) Appl. No.: 10/123,484

(22) Filed: Apr. 17, 2002

(65) Prior Publication Data

US 2002/0108613 A1 Aug. 15, 2002

Related U.S. Application Data

(63) Continuation of application No. 09/501,004, filed on Feb. 9, 2000, now Pat. No. 6,412,487, which is a continuation-in-part of application No. 09/498,705, filed on Feb. 7, 2000, now Pat. No. 6,491,034, and a continuation-in-part of application No. 09/316,227, filed on May 21, 1999, now Pat. No. 6,513,526, and a continuation-in-part of application No. 29/101,860, filed on Mar. 12, 1999, now Pat. No. Des. 428,139, and a continuation-in-part of application No. 29/101,861, filed on Mar. 12, 1999, now Pat. No. Des. 430,663, and a continuation-in-part of application No. 29/101,862, filed on Mar. 12, 1999, now Pat. No. Des. 428,988, and a continuation-in-part of application No. 29/115,618, filed on Dec. 16, 1999, now Pat. No. Des. 443,355.

(30) Foreign Application Priority Data

| Dec. 9, 1998 | (AU) | 3922/98 |
| Dec. 9, 1998 | (AU) | 3923/98 |
| Dec. 9, 1998 | (AU) | 3924/98 |
| Feb. 9, 1999 | (AU) | PP8550 |
| Jun. 18, 1999 | (AU) | PQ1029 |
| Jun. 18, 1999 | (AU) | PQ1040 |
| Jun. 18, 1999 | (AU) | 1916/99 |

(51) Int. Cl.$^7$ ............................................ A62B 18/08
(52) U.S. Cl. ........................... 128/206.24; 128/205.25; 128/207.11
(58) Field of Search ................... 128/205.25, 206.24, 128/206.26, 207.11, 207.13

(56) References Cited

U.S. PATENT DOCUMENTS

| 1,653,572 A | 12/1927 | Jackson |
| 2,931,356 A | 4/1960 | Schwarz |

(List continued on next page.)

FOREIGN PATENT DOCUMENTS

| CA | 88122 | 11/1999 |
| DE | 4 99 00 269.5 | 1/1999 |
| ES | 145309 | 1/2000 |
| FR | 99/16 | 8/1999 |
| GB | 2080119 | 12/1998 |
| GB | 2080120 | 12/1998 |
| GB | 2080121 | 12/1998 |
| JP | 1105649 | 2/1999 |
| SE | 645481 | 8/2000 |

OTHER PUBLICATIONS

Respironcs, Inc. "Nasal Mask System Silicone Countour Mask," Product Instructions, 2 pages, Jun. 1997.

(List continued on next page.)

Primary Examiner—Aaron J. Lewis
(74) Attorney, Agent, or Firm—Nixon & Vanderhye P.C.

(57) ABSTRACT

A respiratory mask assembly includes a rigid mask frame with a rim portion comprising a rearwardly projecting tongue and lateral flange and a cushion having a rim with a corresponding groove and a rearwardly facing shoulder. A clip in the form of a collar passes over the cushion, engaging behind the shoulder, and has securing tabs that engage recesses in the flange.

14 Claims, 19 Drawing Sheets

U.S. PATENT DOCUMENTS

| | | | |
|---|---|---|---|
| 4,807,617 A | | 2/1989 | Nesti |
| 5,003,633 A | | 4/1991 | Itoh |
| 5,243,971 A | * | 9/1993 | Sullivan et al. ........ 128/205.25 |
| 5,538,001 A | | 7/1996 | Bridges |
| 5,794,617 A | | 8/1998 | Brunell et al. |
| 5,909,732 A | | 6/1999 | Diesel et al. |
| 6,082,360 A | | 7/2000 | Rudolph et al. |
| 6,119,693 A | | 9/2000 | Kwok et al. |
| 6,196,223 B1 | | 3/2001 | Belfer et al. |
| 6,412,487 B1 | * | 7/2002 | Gunaratnam et al. .. 128/206.24 |
| 6,463,931 B1 | | 10/2002 | Kwok et al. |
| 6,491,034 B1 | * | 12/2002 | Gunaratnam et al. .. 128/204.18 |
| 2002/0174868 A1 | | 11/2002 | Kwok et al. |

OTHER PUBLICATIONS

ResMed, Mask Systems product Brochure, 2 pages, Sep. 1992.

U.S. patent application Ser. No. 10/164,370, Gunaratnam et al., filed Jun. 10, 2002.

U.S. patent application Ser. No. 09/502,745, Kwok et al., filed Feb. 11, 2000.

U.S. patent application Ser. No. 09/538,349, Gunaratnam, filed Mar. 29, 2000.

U.S. patent application Ser. No. 09/608,440, Kwok et al., filed Jun. 30, 2001.

* cited by examiner

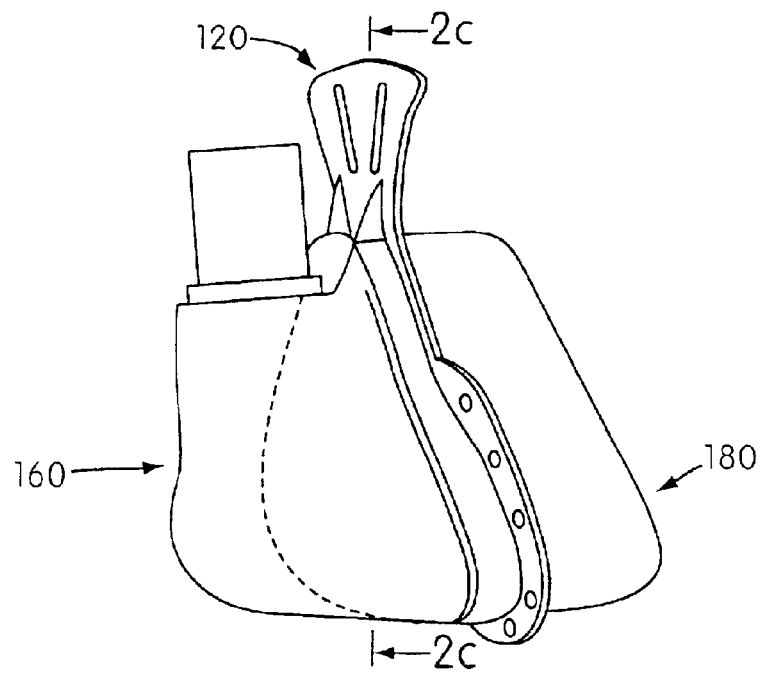
FIG. 2a
PRIOR ART
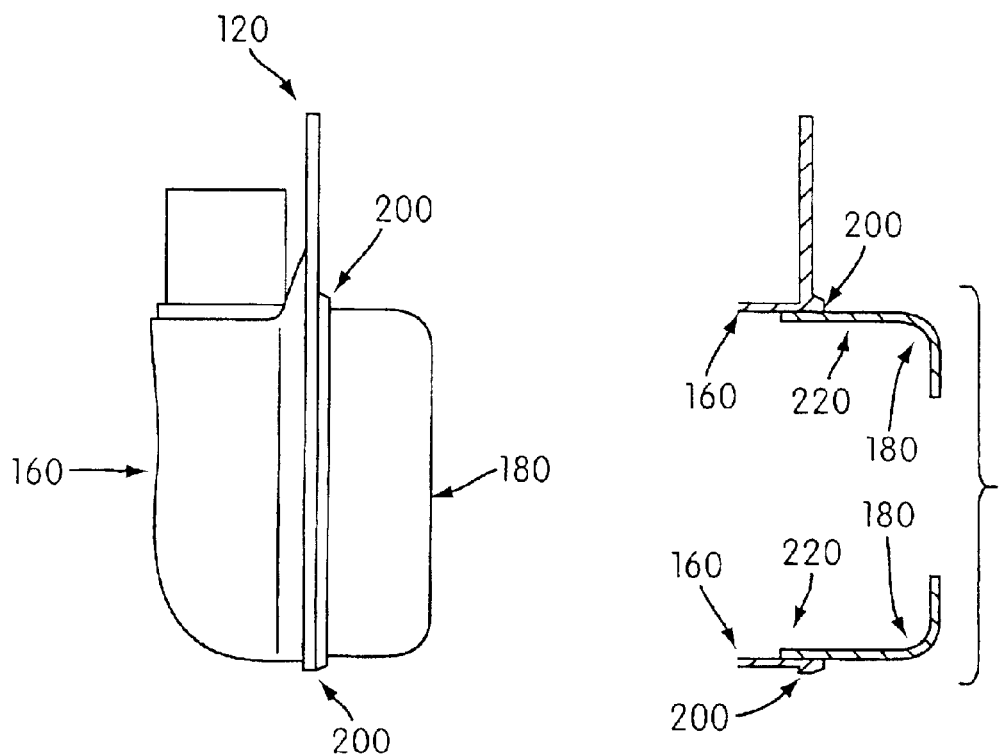
FIG. 2b
PRIOR ART
FIG. 2c
PRIOR ART

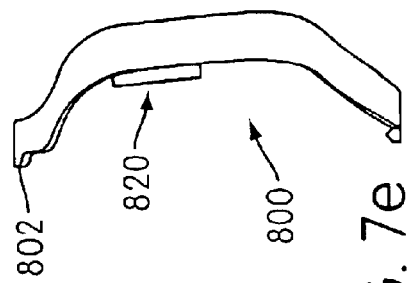
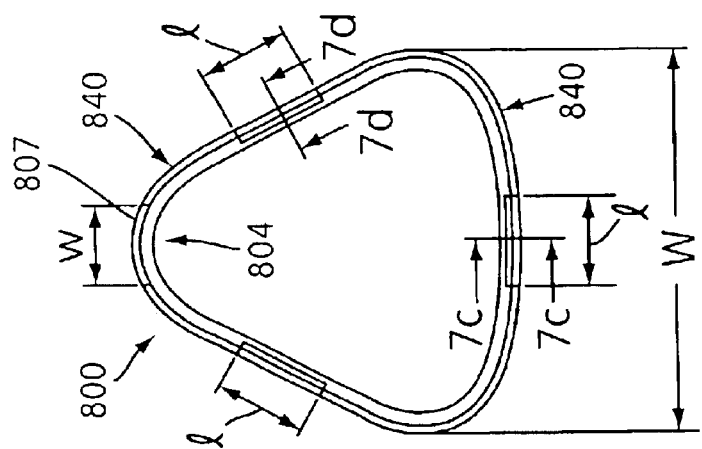
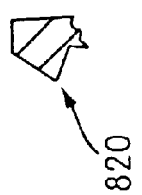
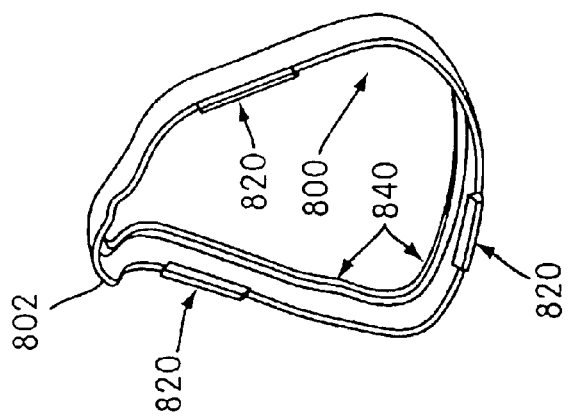
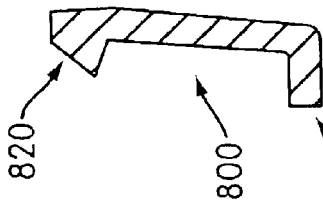

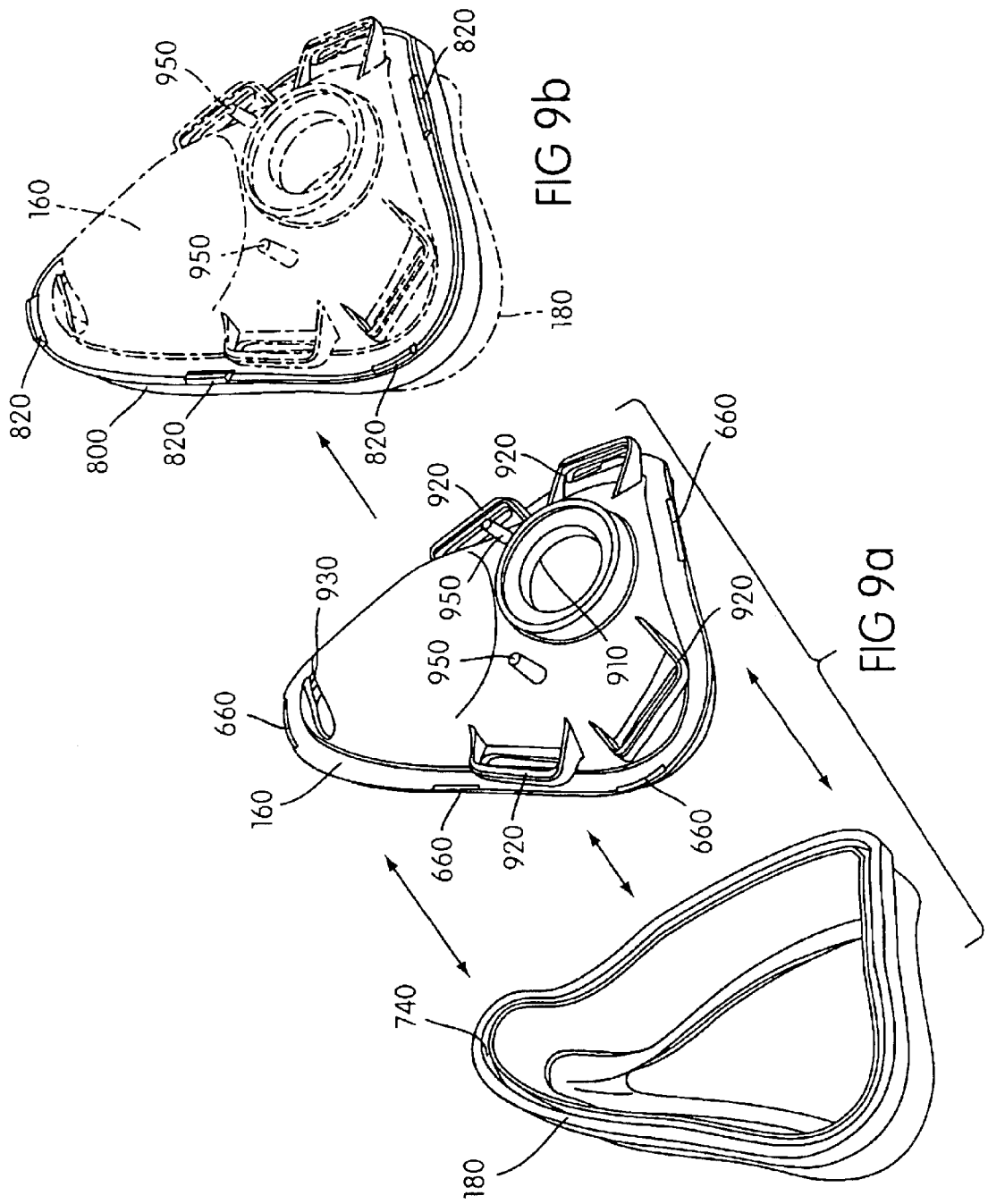

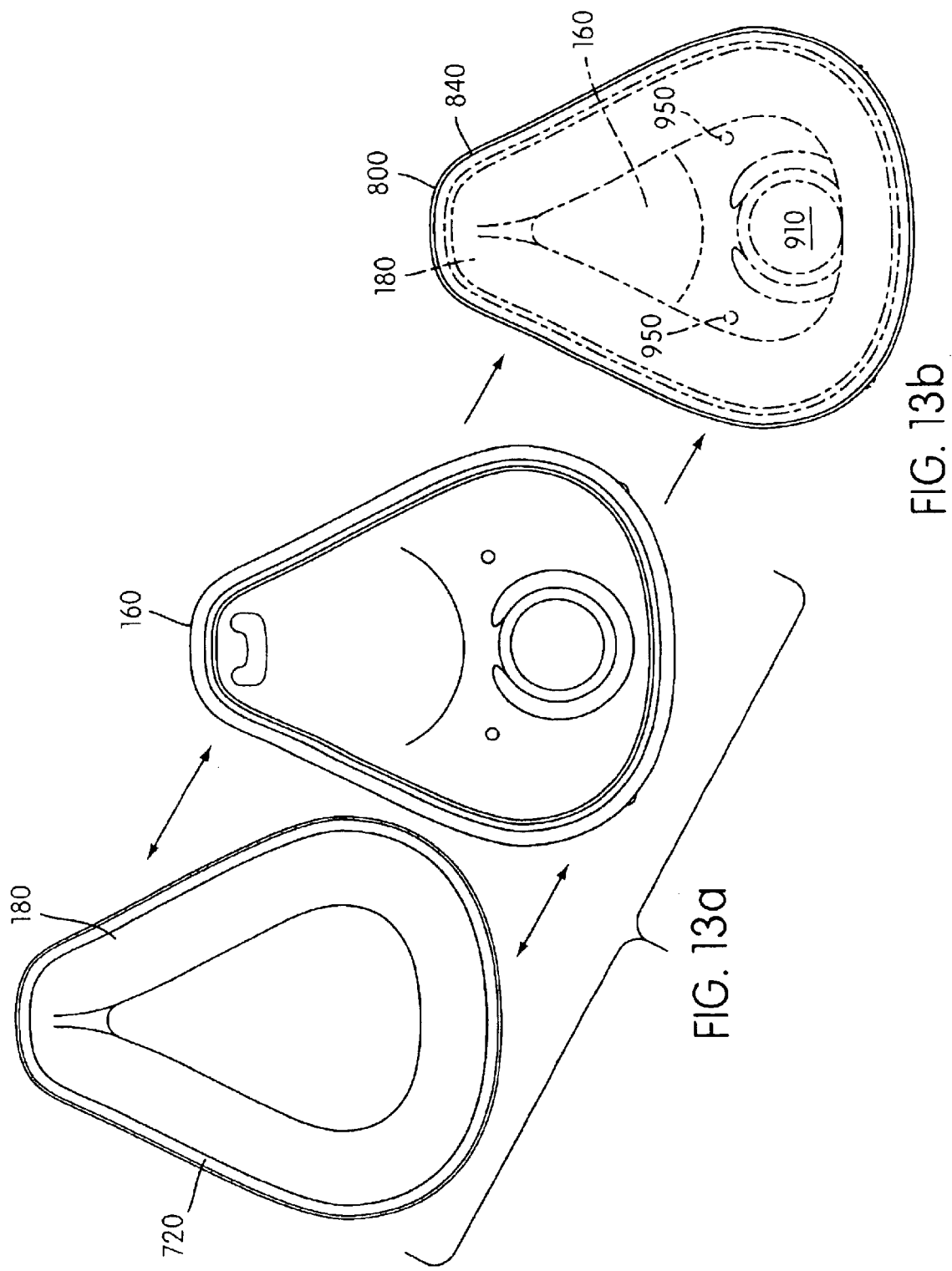

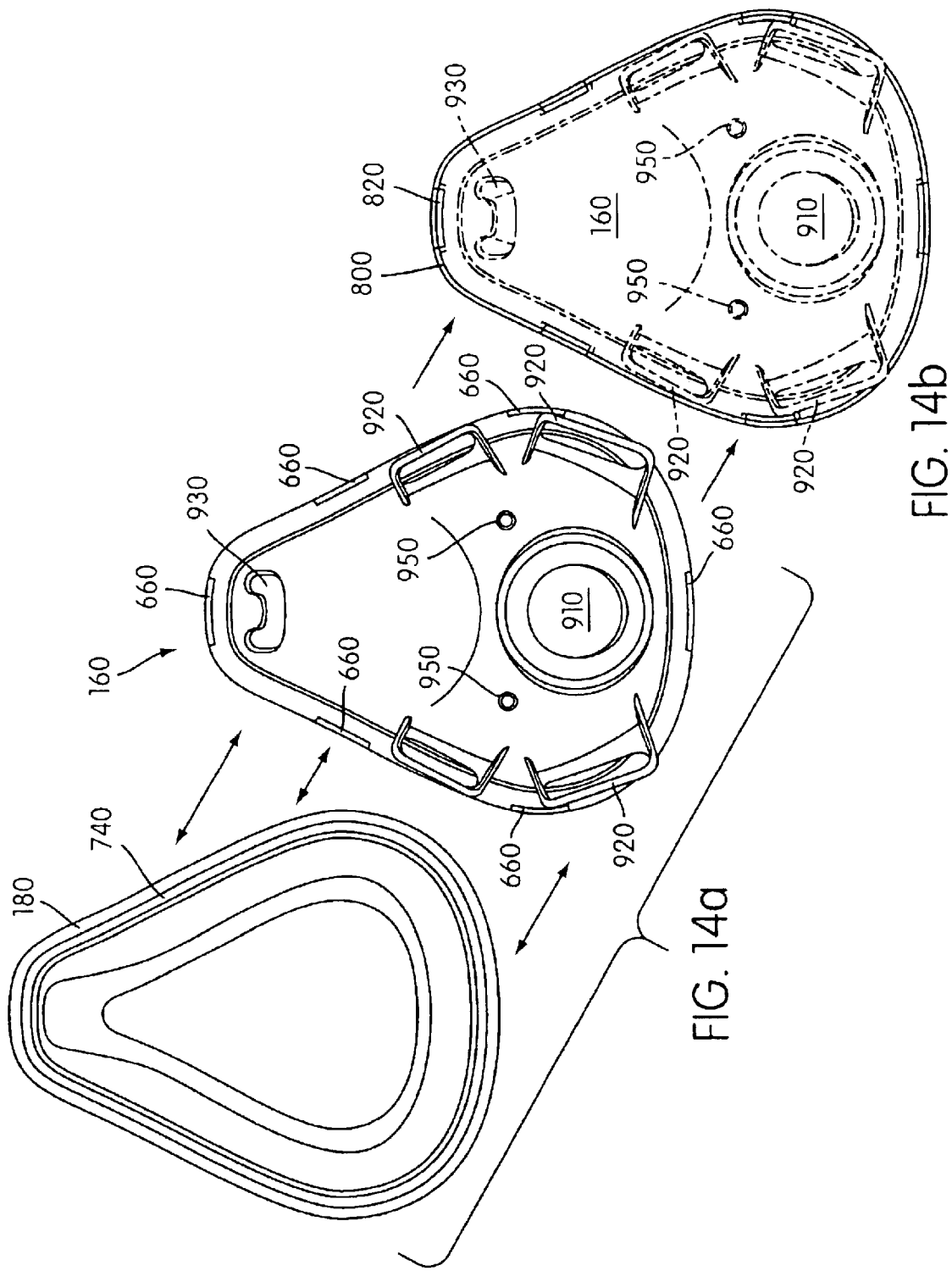

MASK CUSHION AND FRAME ASSEMBLY

This application is a Continuation of U.S. patent application Ser. No. 09/501,004, filed Feb. 9, 2000 now U.S. Pat. No. 6,412,487, allowed, which is a Continuation-in-Part (CIP) of U.S. patent application Ser. No. 09/498,705, filed Feb. 7, 2000 now U.S. Pat. No. 6,491,034, currently pending; a CIP of U.S. patent application Ser. No. 09/316,227, filed May 21, 1999 now U.S. Pat. No. 6,513,526, currently pending; a CIP of U.S. Design patent application Ser. No. 29/101,860, filed 12 Mar. 1999, now U.S. Design Pat. No. D428,139; a CIP of U.S. Design patent application Ser. No. 29/101,861 filed Mar. 12, 1999, now U.S. Design Pat. No. D430,663; a CIP of U.S. Design patent application Ser. No. 29/101,862 filed Mar. 12, 1999, now U.S. Design Pat. No. D428,988; and a CIP of U.S. Design patent application Ser. No. 29/115,618 filed Dec. 16, 1999, now U.S. Design Pat. No. D443,355, the disclosures of which are hereby incorporated by reference.

FIELD OF THE INVENTION

The invention relates to a method and apparatus for connecting a nasal or full-face mask cushion to a mask frame, where the mask is suitable for the delivery of breathable gases to a patient for the treatment of sleep disordered breathing (SDB).

BACKGROUND OF THE INVENTION

Nasal and full-face masks systems suitable for the delivery of air or other breathable gases to patients for the treatment of sleep disordered breathing may include a mask (100), a forehead support (120) and headgear (140), as depicted in FIG. 1. The mask may comprise a rigid shell (160), termed a frame, and a soft portion (180), termed a cushion. The frame may be constructed from a material such as polycarbonate, forming a cavity which overlies the patient's nose and/or mouth. The soft cushion may be constructed from a material such as silicone spacing the frame away from the patient's face to provide comfortable contact.

In the case of the Mirage® Mask (ResMed Limited), shown in FIG. 1, the headgear (140) is constructed from fabric and includes a rear portion which engages the region near the occiput of the patient, and four straps (145) which are secured to a forehead support (2 straps) and nasal mask frame (2 straps). The straps include hook and loop material, such as Velcro(TM) on one side. The mask frame and forehead supports include loops through which straps can pass.

In one form of known mask, the cushion and frame are glued together, as shown in FIG. 2a to 2c. FIG. 2c shows a cross-section 2c—2c through FIG. 2a. The frame (160) includes a rim portion (200) surrounding the rear aperture of the frame. There is a corresponding rim portion (220) on the cushion (180) which fits inside the rim (200) on the frame. The two rims (200, 220) are glued together. A disadvantage with this approach is that the cushion cannot easily be removed for separate cleaning from the frame. Furthermore, there is an increased manufacturing cost since gluing requires assembly time and adhesive.

In one known mask, the Modular mask system (ResMed Limited), the frame and cushion are held together using a tongue (300) and groove (320), as depicted in FIG. 3a to 3c. The frame (160) is generally triangular in font view. In use, the front of the frame faces away from the patient and the back of the frame faces towards the patient. The rim portion (350) on the frame (160) includes an outwardly extending flange (340) and engages with a corresponding rim (360) on the cushion (180), such that the rims (350, 360) confront along a locus lying generally in the plane of the patient's face. The frame rim (350) further includes a tongue (300) which protrudes rearwardly from the back of the frame and is received in a corresponding complementary shaped groove (320) formed in rim portion (360) of the cushion (180). In addition, the rim (350) of the frame (160) and the rim (360) of the cushion (180) include aligned slots (380) through which headgear straps (145) can pess. Hence the slots (380) and straps (145) make a contribution to holding the fame (160) and cushion (180) together, in addition to the use of the tongue (300) and groove (320).

In another known mask, a tongue and groove mechanism is used to hold the frame (160) and cushion (180) together, and the tongue (500), which is positioned on the frame (160) has an irregular cross-section as depicted in FIG. 4a to 4c. The side (520) of the tongue (500) on the interior of the frame (160) is flat. The other side (540) of the tongue (500) has a lateral projection (560) approximately at right angles to the tongue (500). The groove (580) of the cushion (180) has a complimentary shape, including a lateral recess (585) for receiving projection (560). The connection relies on the elasticity of the cushion to retain the cushion in place.

The present invention aims to provide an improved arrangement.

SUMMARY OF THE INVENTION

The present invention provides a respiratory mask assembly for delivering breathable gas to a patient, comprising (i) a substantially rigid mask frame defining a cavity with a rear opening, and a rim portion surrounding said rear opening, said rim portion including a reawardly projecting tongue, (ii) a flexible mask cushion acting to space the mask frame away from the patient's face, said cushion having a rim portion which includes a groove receiving said projecting tongue of the mask frame, and wherein an outer surface of the cushion forms a rearwardly facing shoulder, and (iii) a clip member passing over the mask cushion, having cushion retaining means engaging behind said shoulder of the cushion and securing means which engages the mask frame so as to retain the mask cushion on the mask frame.

Preferably, the clip's securing means includes at least one securing tab which engages a respective recess in the mask frame, and more preferably on a lateral flange of rim portion of the frame.

Preferably also, the clip is formed as a collar member having a plurality of tabs angularly spaced about the collar member, and the mask frame has a respective plurality of the recesses.

BRIEF DESCRIPTION OF THE DRAWINGS

FIG. 2a shows a perspective view of a form of prior art mask frame and cushion which are glued together FIG. 2b shows a side view of the mask shown in FIG. 2a.

FIG. 2c shows a cross-sectional view of the mask shown in FIG. 2a.

FIG. 3b shows aside view of the mask shown in FIG. 3a.

FIG. 3c shows a cross-sectional view of the mask shown in FIG. 3a.

FIG. 5b shows a side view of the mask frame shown in FIG. 5a.

FIG. 6e shows a view from the patient (rear) side of the mask cushion shown in FIG. 6a.

FIG. 7a shows a perspective view of a clip suitable for the nasal mask frame of FIGS. 5a and 5b and the nasal mask cushion of FIGS. 6a to 6f.

FIG. 7b shows a view of the clip shown in FIG. 7a.

FIG. 7c shows an enlarged section 7c—7c through the clip in the position indicated in FIG. 7b.

FIG. 7d shows an enlarged section 7d—7d through the clip in a position indicated in FIG. 7b.

FIG. 7e shows a side view of the clip shown in FIG. 7b.

In FIGS. 6a to 6f and 7a to 7e dimensions are shown in millimeters.

FIG. 9a is a front perspective exploded view illustrating the cushion and frame according to the full face mask embodiment.

FIG. 9b is an assembled view of the cushion and frame, along with the clip.

FIG. 13a is an exploded rear view of the frame and cushion according to the full face mask.

FIG. 13b is an assembled view of the cushion and frame, along with the clip.

FIG. 14a is an exploded front view of the frame and cushion according to the full face mask.

FIG. 14b is an assembled view of the cushion and frame, along with the clip.

DETAIL DESCRIPTION OF THE INVENTION

The method and apparatus for securing a cushion to a mask frame includes a combination of tongue and groove mechanism and a clip in the form of a collar member which passes over and engages both the cushion and the frame.

Figure 5A:
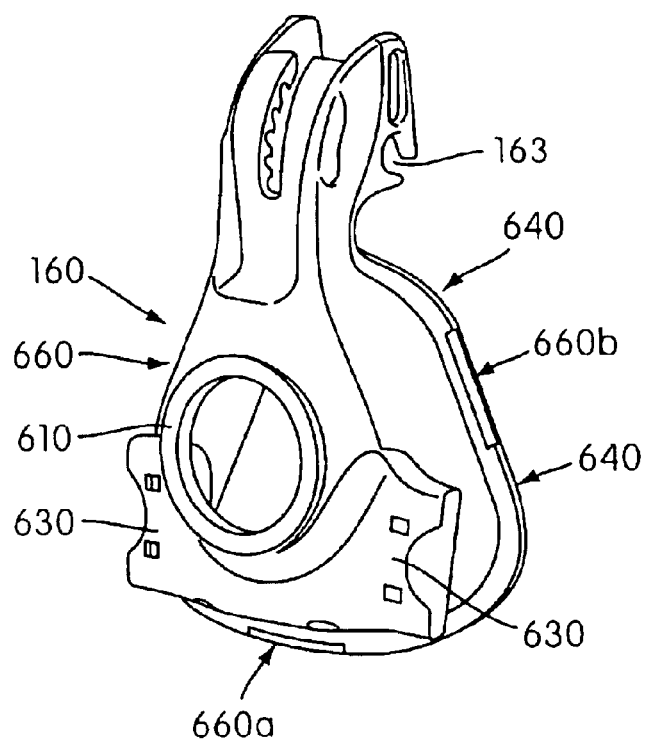
FIG. 5a shows a front perspective view of a nasal mask frame according to an embodiment of the invention.
Figure 5B:
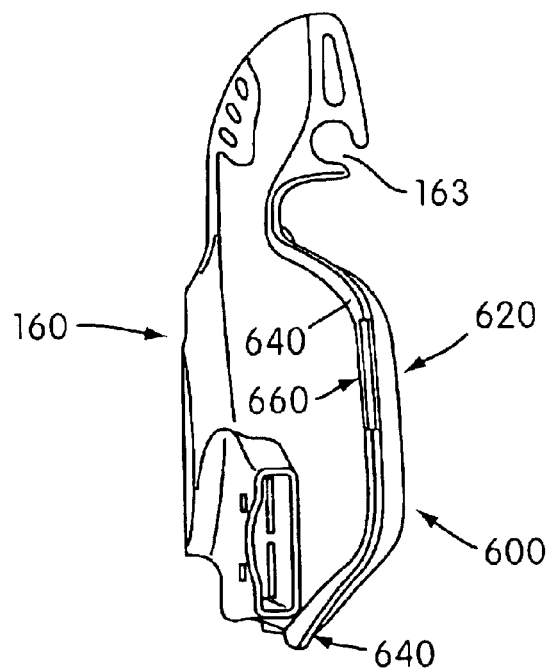
Figure 5C:
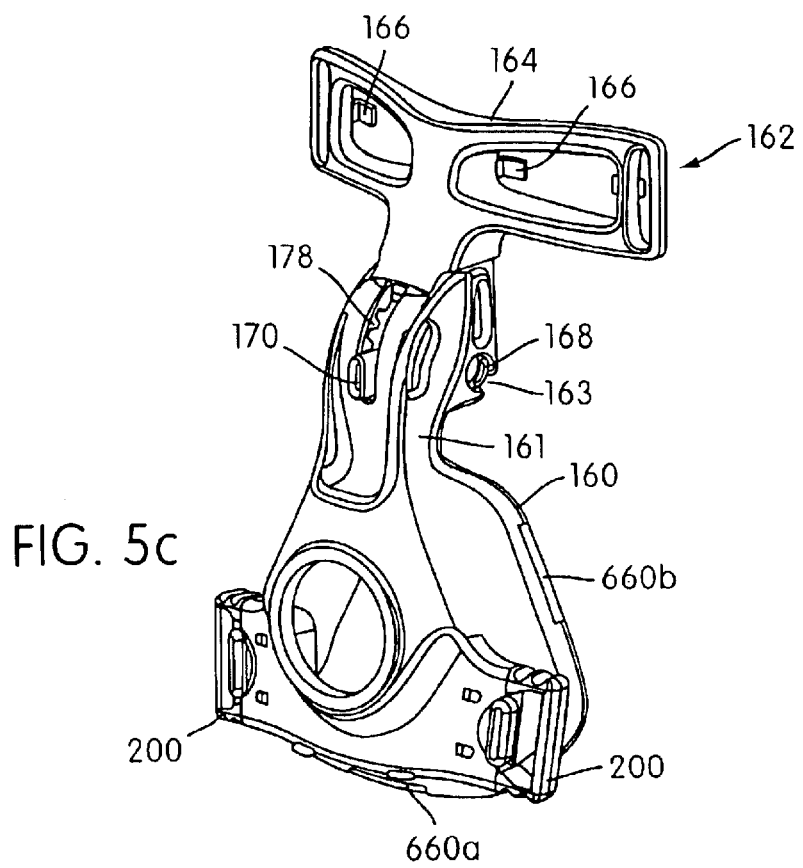
FIG. 5c is a front perspective view of a nasal mask frame and adjustable forehead support according to an embodiment.
Figure 5D:
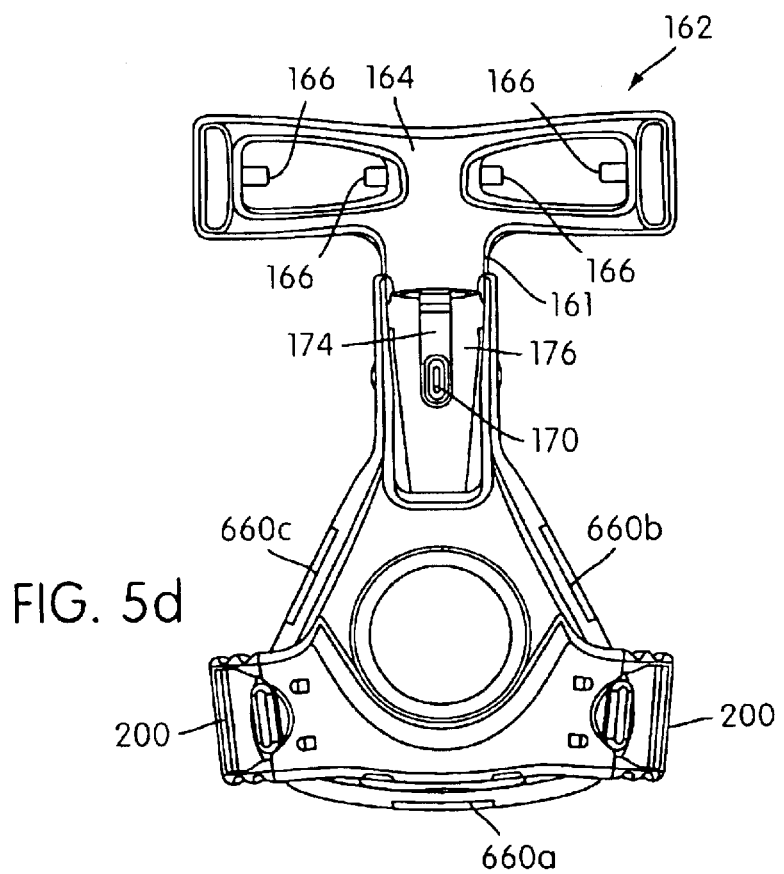
FIG. 5d is a front view of the embodiment of FIG. 5c.
Figure 5E:
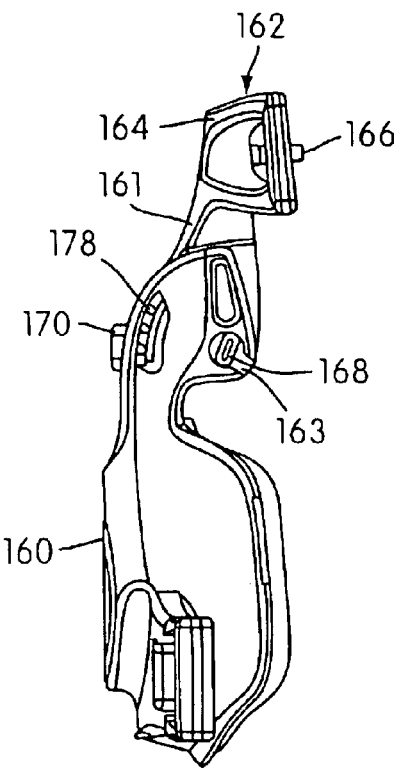
FIG. 5e is a side view of the embodiment of FIG. 5c.

A nasal mask frame including a rim portion according to an embodiment of the invention is shown in FIG. 5a and FIG. 5b. The frame (160) is constructed as a substantially rigid shell of polycarbonate or similar transparent plastics material, and incorporates a gas inlet aperture (610) for connection to a gas delivery conduit (not shown) of a patient gas delivery system.

The frame (160) is generally triangular in front view, covering the patient's nose, and defines a cavity which is open at its rear, the rear opening being surrounded by a rim portion (600) which follows a locus approximating the contours of a patient's face.

On the front surface of the frame, are strap connection points (630) for connection of the mask to patient headgear. Connectors (200) are shown in FIGS. 5c–5f.

As best seen in FIG. 5b, the rim portion (600) of the frame (160) includes a rearwardly projecting tongue (620) and a lateral flange (640). The tongue (620) has an approximately rectangular cross-section. The flange (640) is approximately perpendicular to the tongue (620) and also has an approximately rectangular cross-section. The flange (640) includes three recesses (660) angularly spaced about the rim. Of these, only the bottom recess (660a) and one side recess (660b) are visible in the view of the frame (160) shown in FIG. 5a. The recesses are of an approximately rectangular shape, formed in the front surface of flange (640) adjacent its edge.

FIGS. 5c–5f show additional views of the frame (160). As compared to FIGS. 5a–5b, FIGS. 5c–5f also show an adjustable forehead support (162) connected to the frame (160). The adjustable forehead support (162) includes a bridge portion (164) adapted to locate at least one and preferably two spaced apart pads (not shown) adapted to contact the forehead of the patient. Projection members (166) are formed on the bridge portion (164), and can be used to secure the forehead pads to the bridge portion (164).

The forehead support (162) is coupled to the frame (160) in this example using a pair of small shafts (168) formed on the forehead support (162). The frame (160) includes an extension (161) having a pair of keyed receiving slots (163) to receive the shafts (168). Adjustment is carried out by use of an actuator button (170) coupled in cantilever fashion to the end of a tab (172) formed on the forehead support (162). The actuator button (170) protrudes from the patient side of the extension (161) through a slot (174) (FIG. 5d) formed in the extension (161), thereby exposing the actuator button (170) to the exterior surface (176) of the extension (161), which facilitates access by the patient. The frame (160) is provided with a number of teeth (178), e.g. at least three, to enable the forehead support (162) to be positioned in a corresponding number of positions, so the mask can accommodate patients having a wide scope of facial geometries.

Figure 5F:
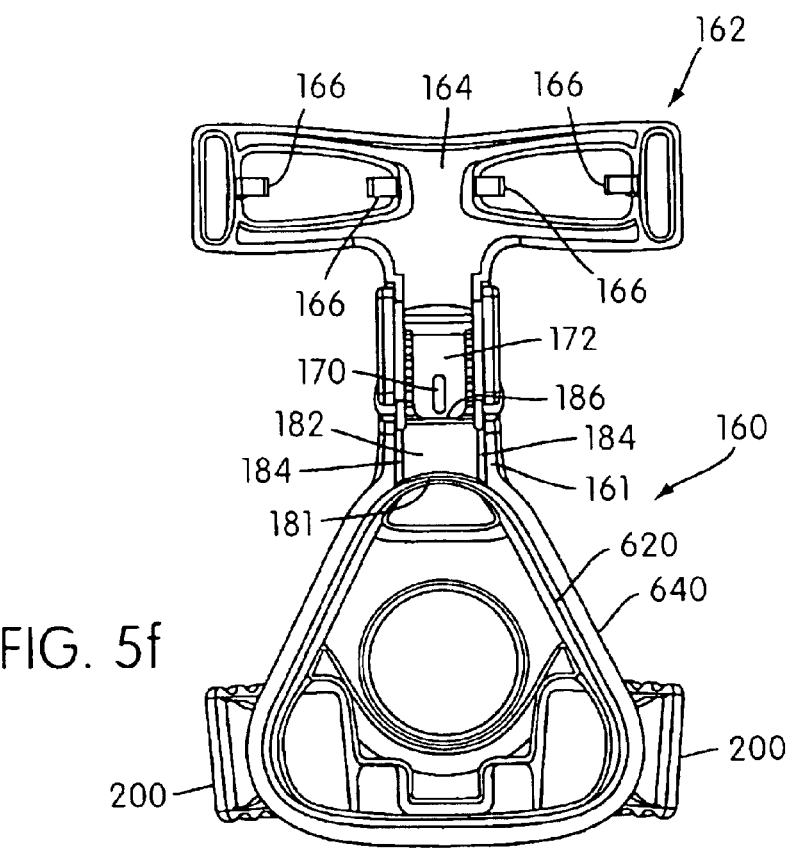
FIG. 5f is a rear view of the embodiment of FIG. 5c.

FIG. 5f shows that the tongue (620) and the flange (640) have a generally triangular shape. An apex (181) of the tongue (620) is provided adjacent to a point where the extension (161) extends upwardly above the main part of the frame (160). A receiving space (182) is defined in a region of the extension (161) just above the apex (181) of the tongue (620). Sidewalls (184) define the side boundaries of the receiving space (182), while the end (186) of the tab (172) defines the upper boundary of the receiving space (182). The purpose of the receiving space (182) will be described below in conjunction with FIGS. 7a–7e.

A nasal mask cushion including a rim portion (700) according to an embodiment of the invention is shown in FIGS. 6a to 6f. The front edge of the rim portion (700) has a groove (740) which is of complementary shape to and closely receives the tongue (620) of the frame (160).

The thickened rim portion (700) of the cushion has an inwards step (720) in its outer surface, forming a rearwardly facing shoulder.

Figure 6C:
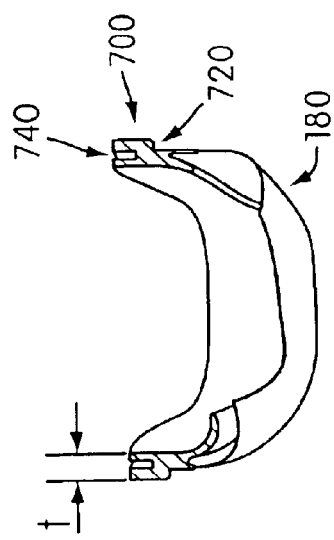
FIG. 6c shows a cross-section through the mask cushion shown in FIG. 6e.
Figure 6B:
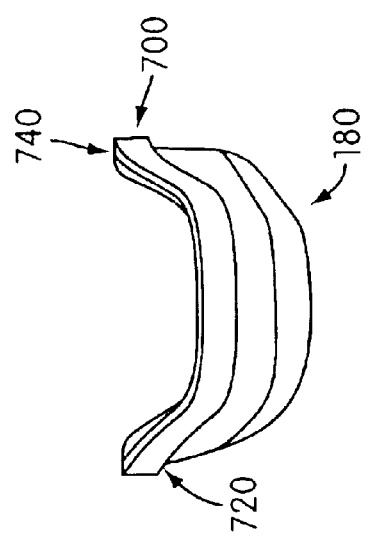
FIG. 6b shows a side view of the mask cushion shown in FIG. 6e.
Figure 6A:
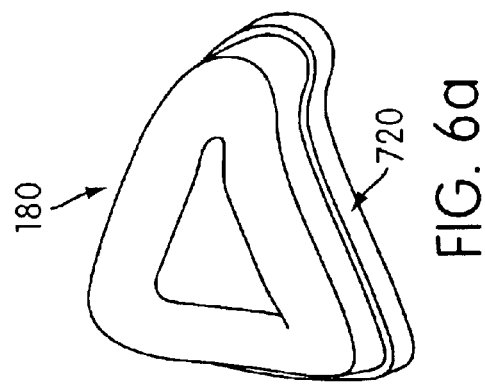
FIG. 6a shows a rear perspective view of a nasal mask cushion suitable for the nasal mask frame of FIGS. 5a and 5b.
Figure 6F:
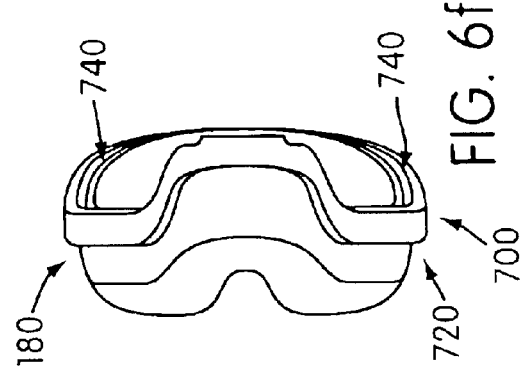
FIG. 6f shows a top view of the mask cushion shown in FIG. 6e.
Figure 6E:
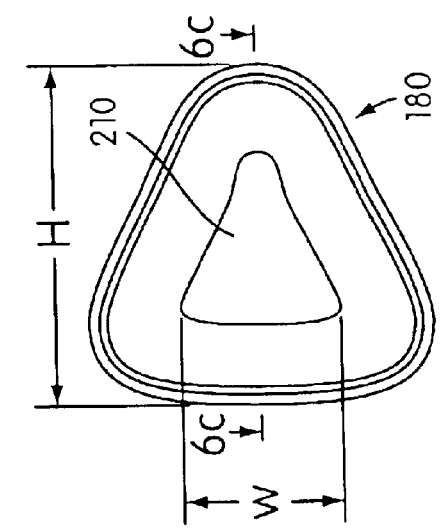
Figure 6D:
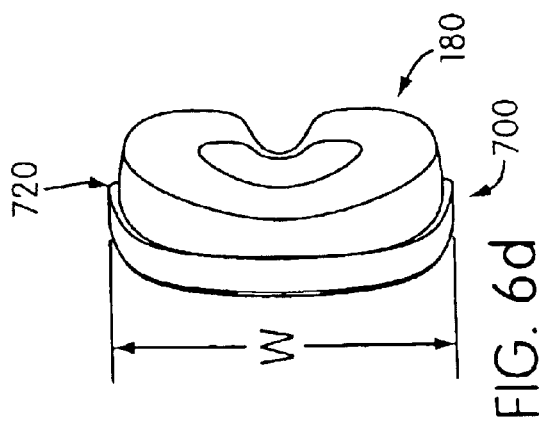
FIG. 6d shows a bottom view of the mask cushion shown in FIG. 6e.
Figure 8A:
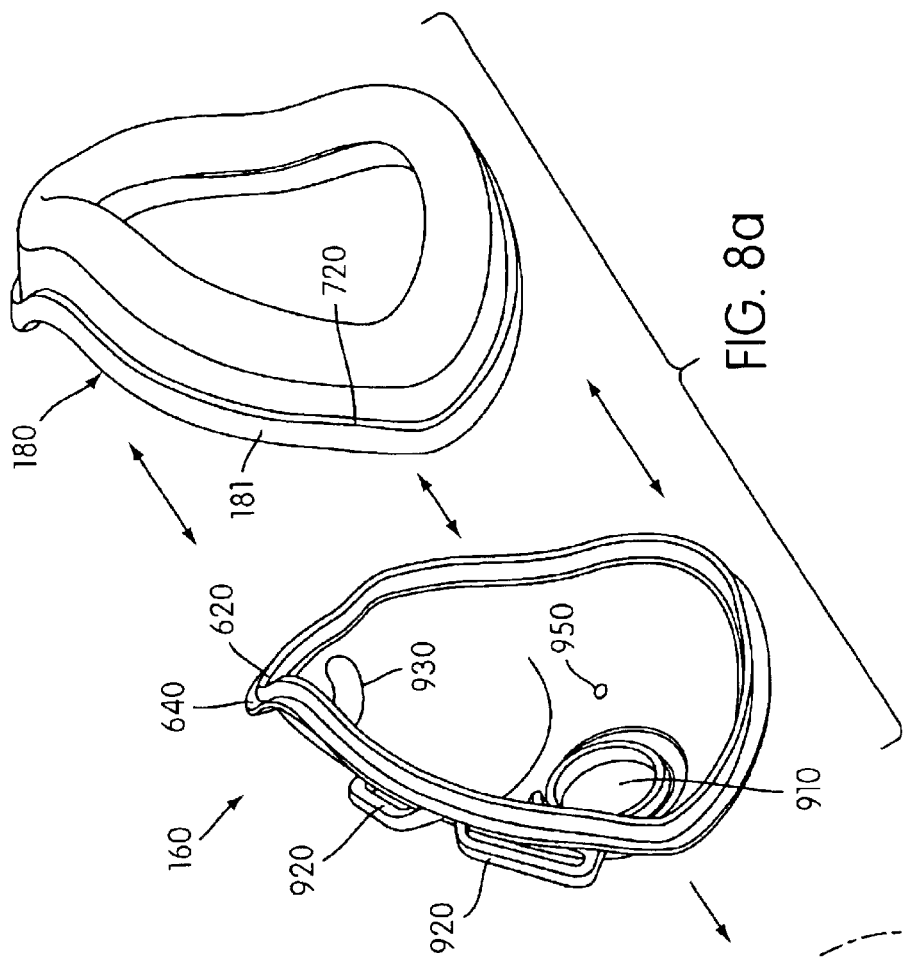
FIG. 8a is a rear perspective exploded view illustrating the cushion and frame according to a full face mask embodiment.
Figure 8B:
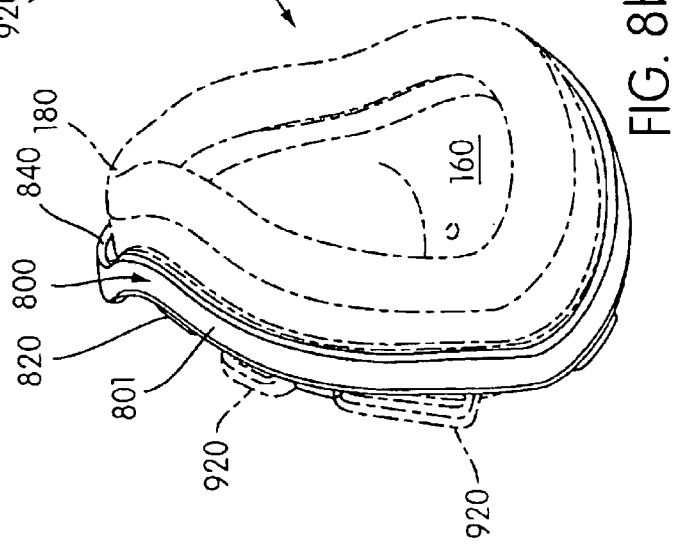
FIG. 8b is an assembled view of the cushion and frame of FIG. 8a, along with the clip.
Figures 10A, 10B:
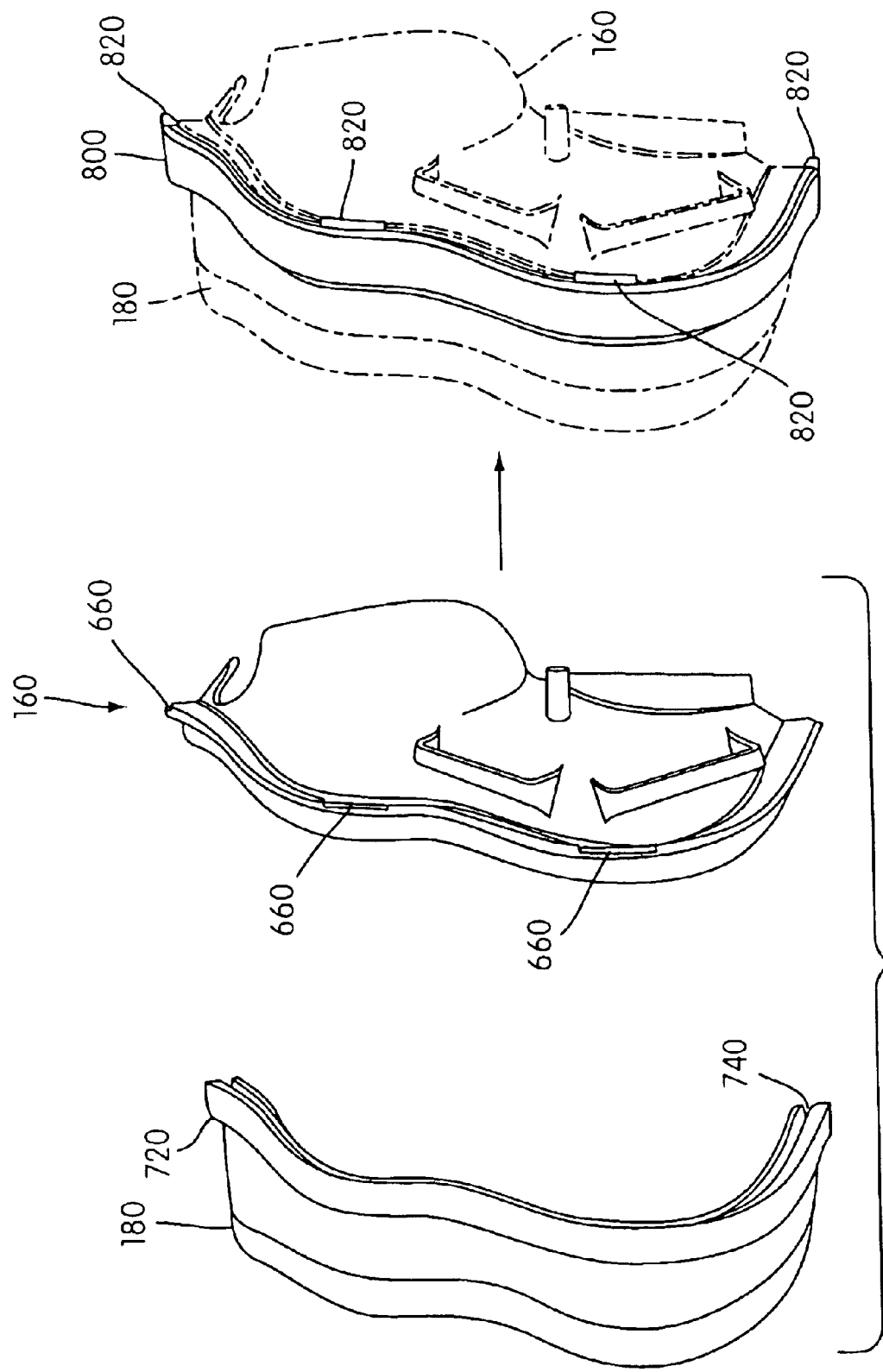
FIG. 10a is an exploded side view of the cushion and frame according to the full face mask embodiment.
FIG. 10b is an assembled view of the cushion and frame, along with the clip.
Figure 11B:
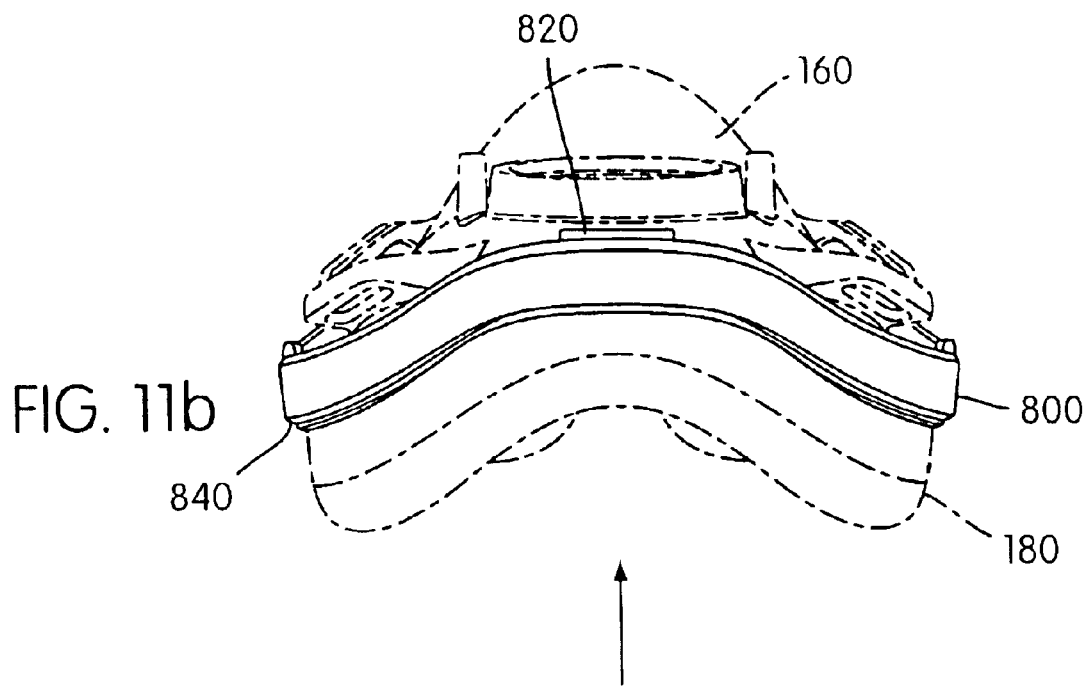
FIG. 11b is an assembled view of the cushion and frame, along with the clip.
Figure 11A:
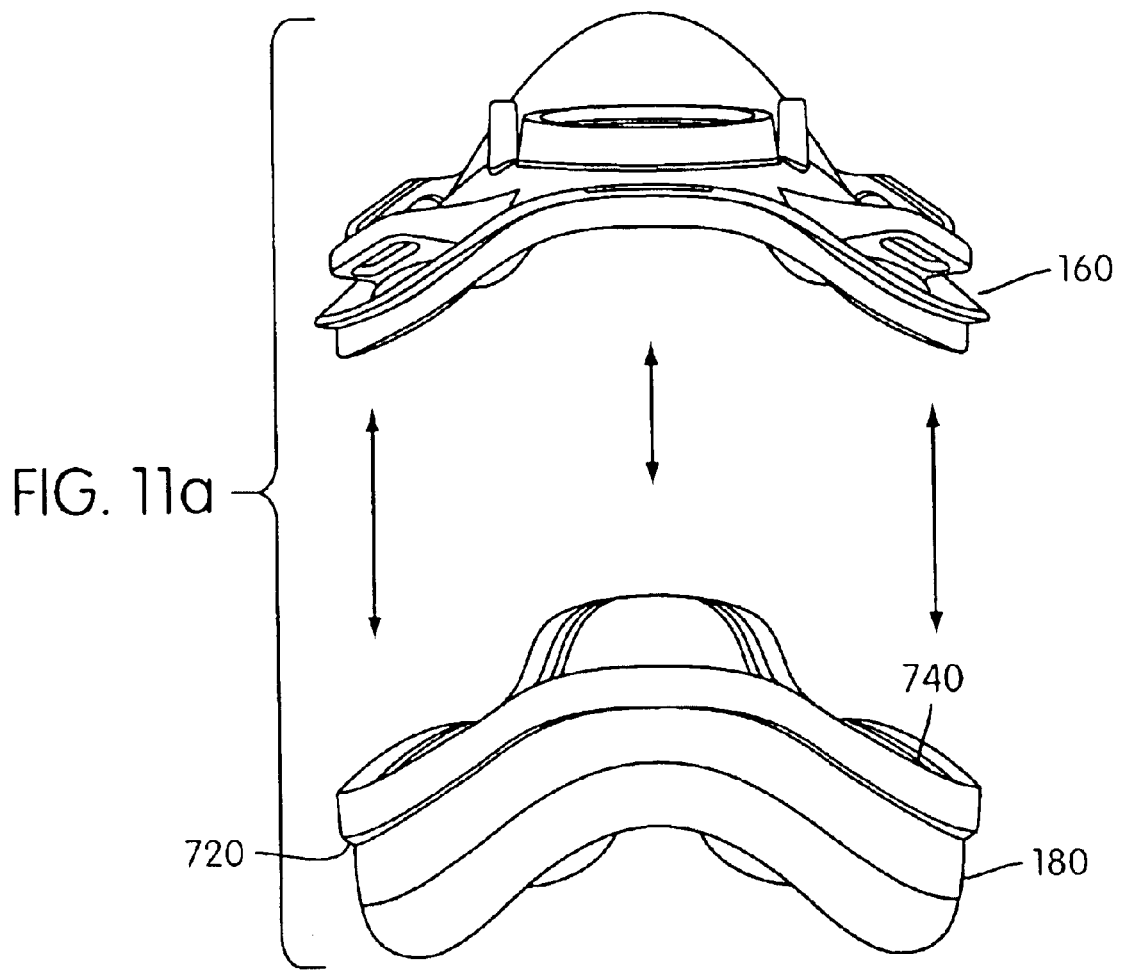
FIG. 11a is an exploded bottom view of the frame and cushion according to the full face mask.
Figure 12B:
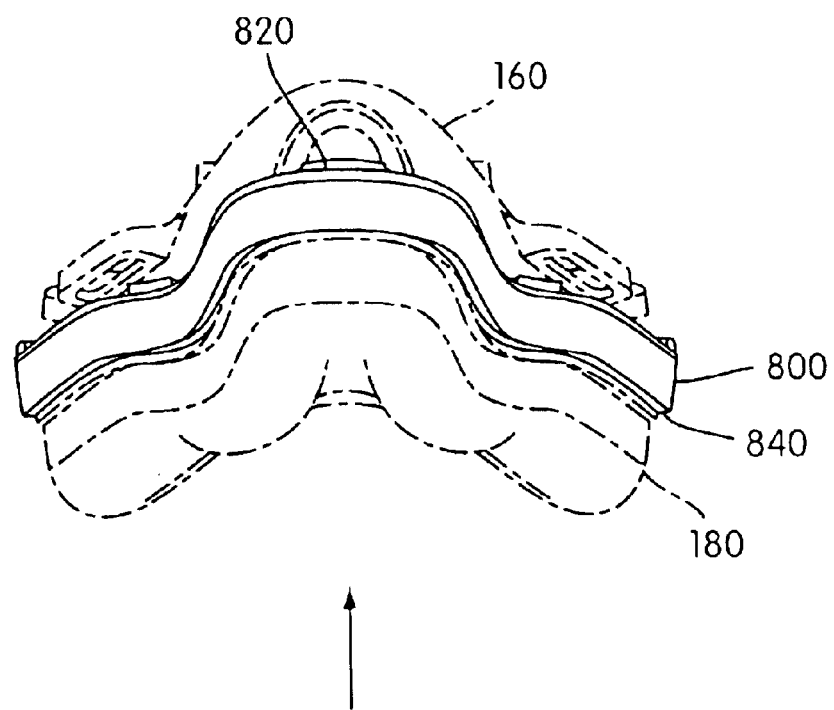
FIG. 12b is an assembled view of the cushion and frame, along with the clip.
Figure 12A:
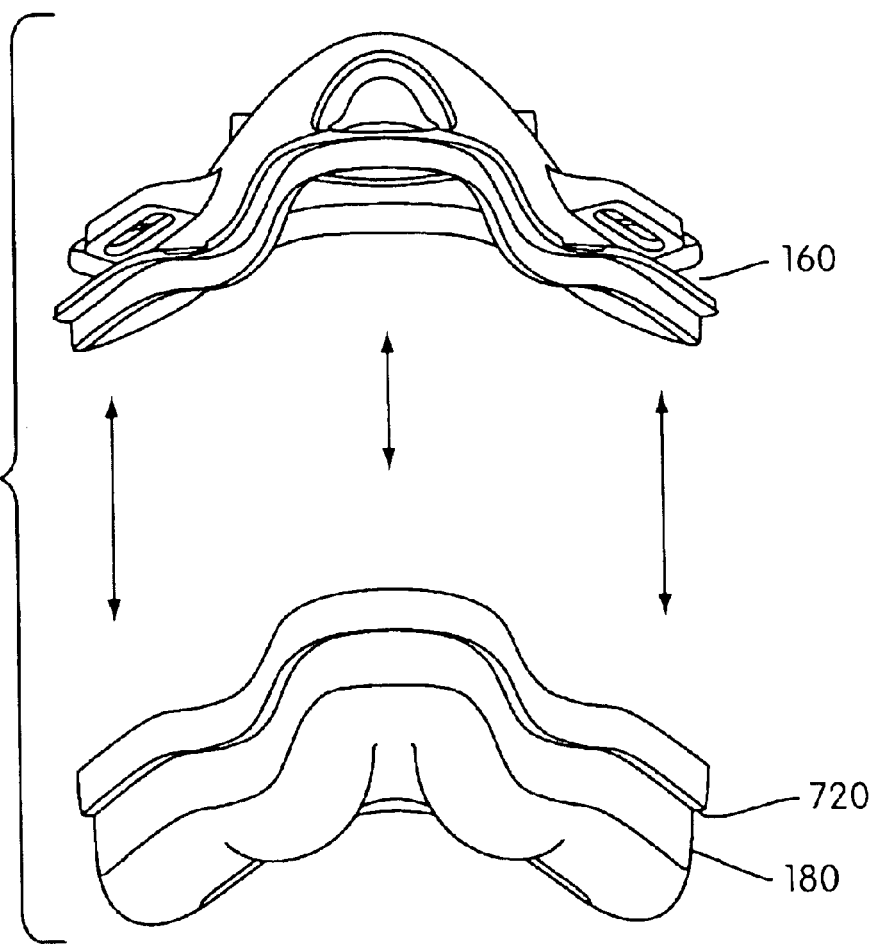
FIG. 12a is an exploded top view of the frame and cushion according to the full face mask.

The cushion is formed of soft material such as silicone, and projects rearwardly of the mask frame so as to space the rigid frame away from the patient's face. The width (W) of the cushion is about 71.2 mm, as shown in FIG. 6d. The width (W) of the aperture 210 is about 31.7 mm. The height (H) is about 72.1 mm. The height of the aperture 210 is about 36.7 mm. The thickness (t) of the lower sidewall is about 6.6 mm., as shown in FIG. 6c.

A clip (800) according to an embodiment of the invention, suitable for a nasal mask, is shown in FIG. 7a to 7e. The clip is formed as a collar of a complementary shape to the rims of the mask cushion (700) and frame (600) and fits over them. The clip is conducted from polycarbonate or similar material. In the illustrated embodiment the clip (800) includes three securing tabs (820) such that inwards projections on the detents are formed as resilient detents which extend past the outer edge of flange (640) to be retained in recesses (660) on the front of the flange (640). To disengage, for example for cleaning of the mask assembly or replacement of the cushion, the detents may be forced outwardly against their natural resilience to release from the recesses (660) and ride over the outer edge of flange (640). In other embodiments, other numbers of securing tabs may be used.

The rear of the clip has an inwards flange (840) which engages behind the shoulder (720) of the cushion so as to hold the cushion securely in position on the frame when the tabs (820) are engaged on the rim (600) of the frame.

Furthermore, the clip (800) includes a guide projection (802) located at an apex (804) of the clip (800), as shown in FIGS. 7a, 7b and 7e. The projection (802) is positioned diametrically across from the lowermost securing tab (820), as best seen in FIG. 7b. The projection (802) has an actuate shape that generally matches the curve of the clip (800) at the apex (804) thereof.

As shown in FIG. 7b, the length (1) of each of the securing tabs is about 18.0 mm. The width (w) of the guide projection (802) is about 15.5 mm, and the width (W) of the base of the clip (800) is about 73.83±0.5 mm.

The guide projection (802) helps guide the clip (800) into place when the clip (800) is secured to the frame (160). In this context, the guide projection (802) is not shown as including inwardly facing detents, which distinguish the guide projection (802) from the securing tabs (820), which have inwardly facing detents. In particular, the guide projection (802) is intended to be received within the receiving space (182), which is shown in FIG. 5f. The guide projection (802) has a shape that is complementary to the shape of the apex (181) of the tongue (620) of the frame (160). The width (w) of the guide projection (802) is dimensioned such that it fits between sidewalls (184) of the extension (161).

Figure 15:
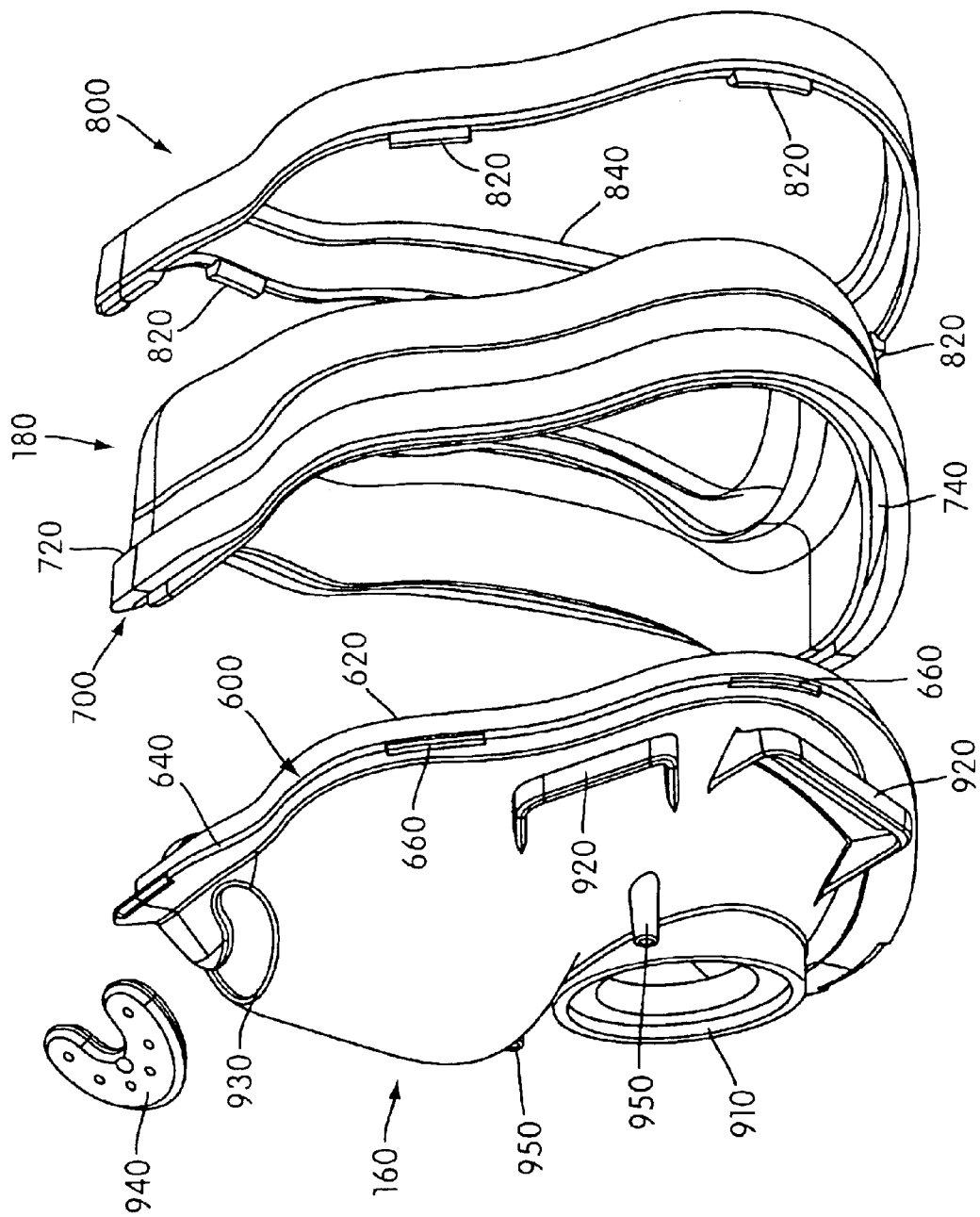
FIG. 15 is an exploded view of an embodiment of the invention as a full-face masks.
Figure 16A:
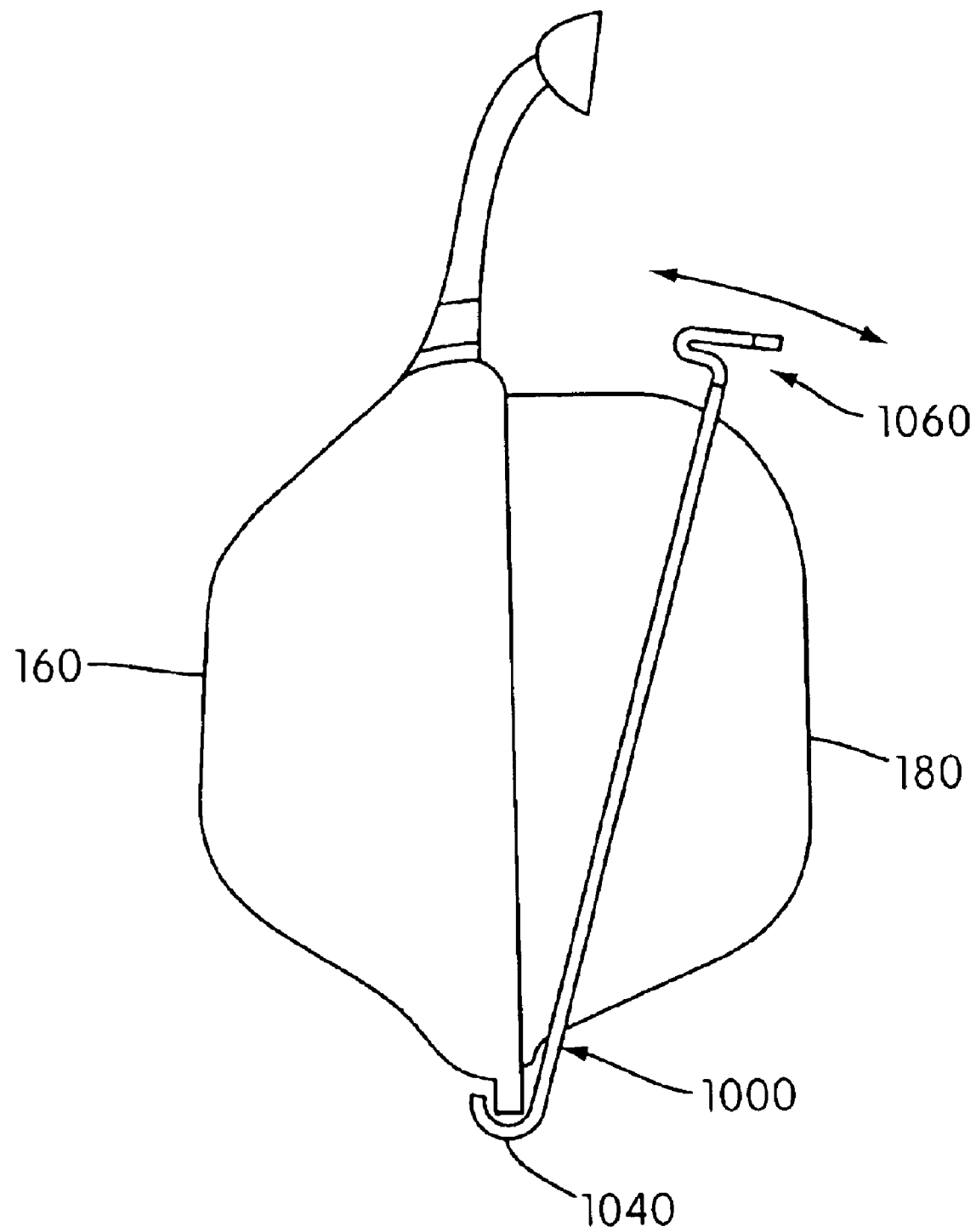
FIG. 16a is a schematic side view of an embodiment employing an alternative clip arrangement.
Figure 16B:
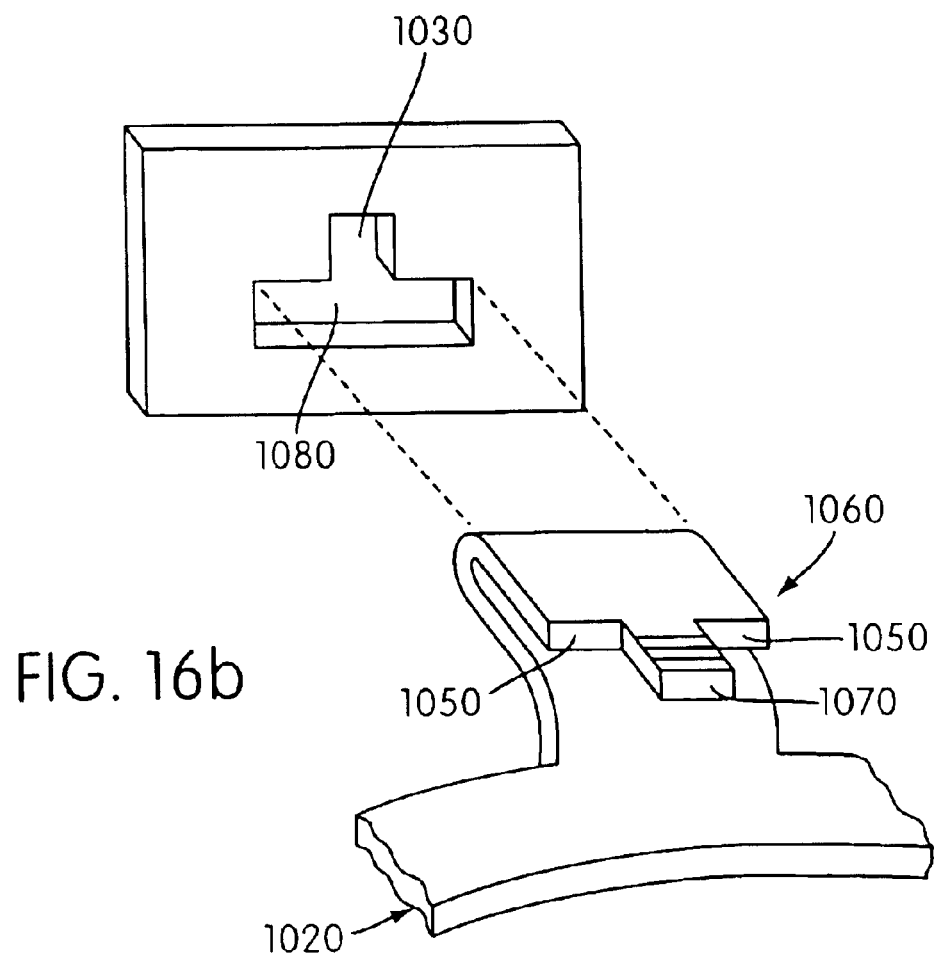
FIG. 16b is a perspective view of engagement of the clip with the mask frame.
Figure 16C:
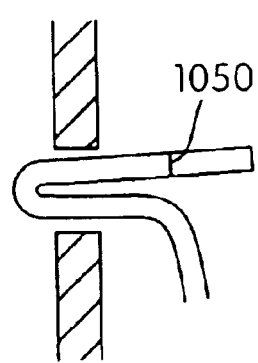
FIG. 16c and 16d are side views showing clipping of the tab into the slot on the mask frame.
Figure 16D:
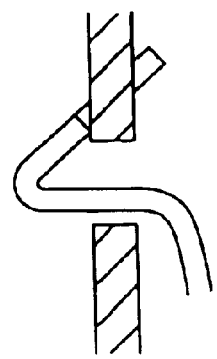

The invention is also suitable for a full-face mask system. FIGS. 8a–15 show several exploded views of a Mirage® full-face mask which includes an embodiment of the invention, including a mask frame (160), cushion (180) and clip (800). While FIGS. 8a, 9a, 10a, 11a, 12a, 13a and 14a show an exploded view of the frame (160) and the cushion (180), FIG. 15 shows an exploded view including the clip (800) as well. FIGS. 8b, 9b, 10b, 11b, 12b, 13b and 14b show the assembled view of the cushion, clip and frame, with the cushion and frame shown in phantom and the clip shown in solid lines. The clip (800) in FIG. 8b can be seen to overlie the cushion (180) since a sidewall (801) of the clip (800) instead of the sidewall (181) of the cushion (180) is visible. In addition, at least one of the securing tabs (820) can be seen. In FIGS. 9a–12a and 14a, recesses (660) can be seen on the frame (160), and FIGS. 9b–12b and 14b show the securing tabs (820) which engage with the recesses (660). FIG. 14b in particular shows that the clip (800) completely surrounds the frame (160), and each of the securing tabs (820) is positioned within respective recesses (660). FIG. 14b also shows that the recesses (660) are slightly larger than the securing tabs (820) in length so as to allow for a small degree of misalignment, to facilitate assembly. The frame (160) is adapted to cover both the mouth and nose region of the patient's face, and includes a gas inlet aperture (910), connection points (920) for headgear straps, an aperture (930) for receiving an air vent (940) (FIG. 15) and ports (950).

The interengagement of the clip (800) and the respective rim portions (600), (700) of the frame (100) and cushion (180) are similar in principle and construction to those described above with reference to FIGS. 5a to 5f, 6a to 6f and 7a to 7e, except there are six angularly spaced tabs (820) and the respective recesses (660). As in the nasal mask assembly, the rim portion (600) of the frame includes a tongue (620) and a lateral flange (650) with recesses in its front surface adjacent its edge, the rim portion (700) of the cushion having a complementary groove (740) and rear shoulder surface (720), and the clip having a flange (840) and securing tabs (820) generally as described above for the nasal mask assembly.

FIGS. 16a to 16d illustrate an alternative clipping arrangement. The clip (1000) is again formed generally as a collar, with a rear flange (1020) for engaging the shoulder of the cushion as previously described.

At the base of the clip is a securing hook (1040) which hooks over and engages behind the lateral flange of the mask frame (160), allowing the clip to pivot.

At the top of the clip is a resilient detent arrangement (1060), adapted for engagement with an inverted T-shaped slot (1080) on the upper extension of the mask frame (160) as best shown in FIGS. 9a to 9c.

As shown, the detent is formed as a resilient U-shape with rearwardly facing shoulders (1050) either side of a narrow tab (1070). In use, the clip is pivoted to force the U-shaped detent through the wide part of the T-slot (1080), until the shoulders (1050) clear the rear surface of the slot. The resilience of the detent then forces tab (1070) into the leg (1030) of the T-slot, to retain the clip in position. To disengage the clip, the tab (1070) is depressed to allow the detent to pass back through the slot.

Figure 1:
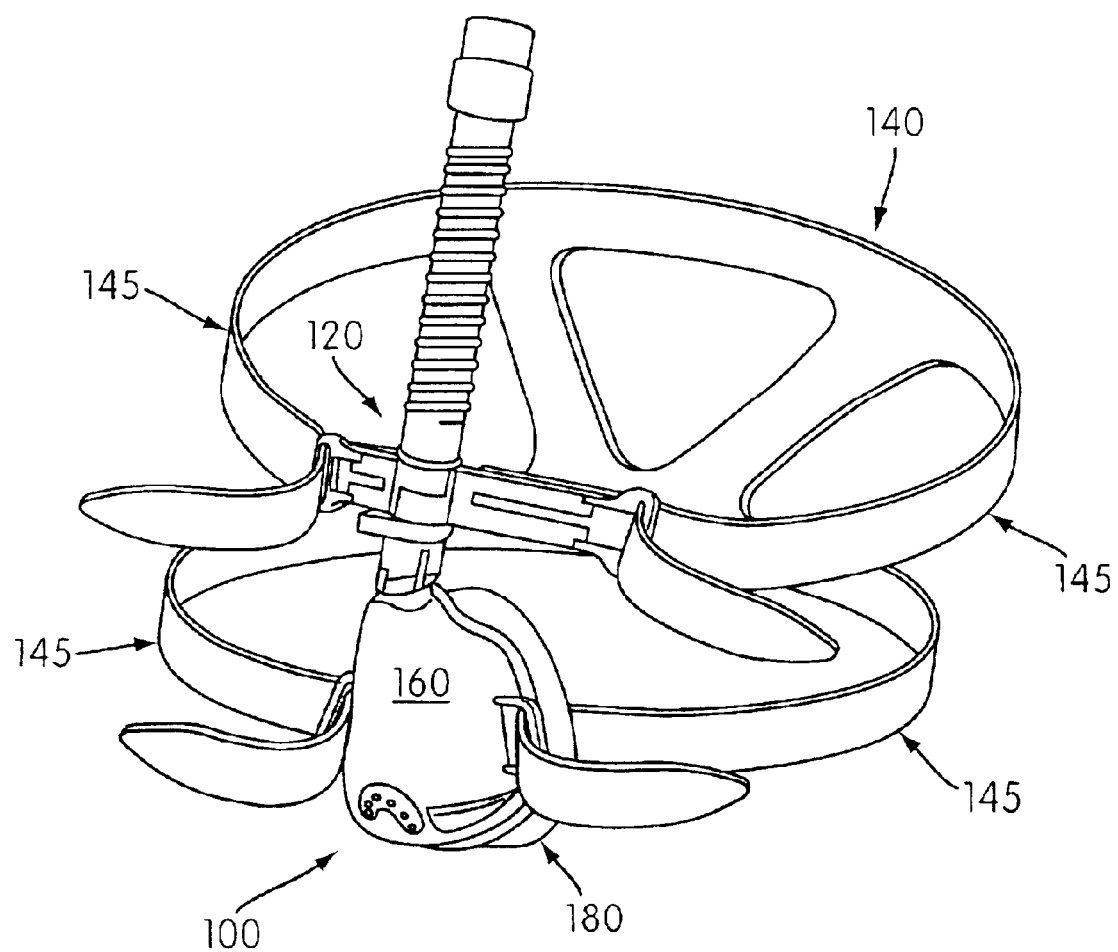
FIG. 1 shows the prior art Mirage® nasal mask system including mask frame, cushion, headgear and forehead support.
Figure 3A:
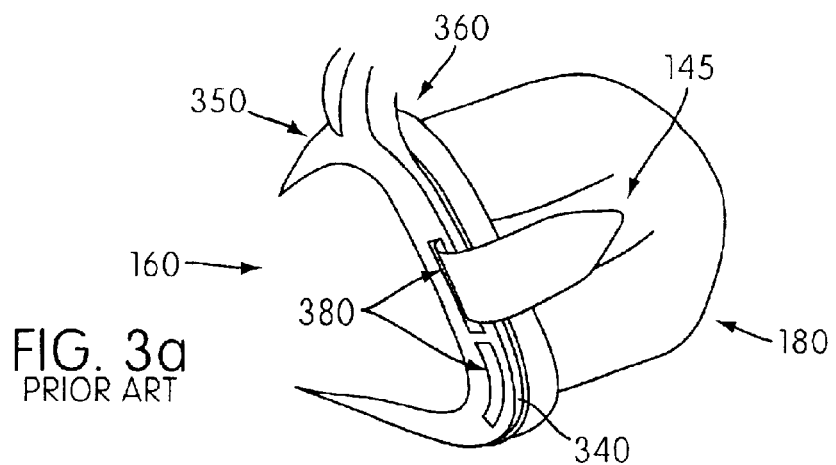
FIG. 3a shows a perspective view of the mask frame and cushion and strap of the prior art ResMed Modular Mask System.
Figure 3B:
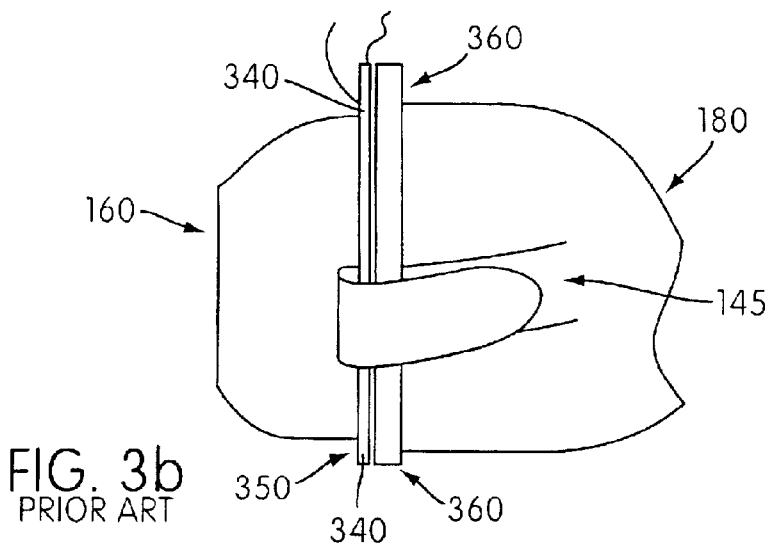
Figure 3C:
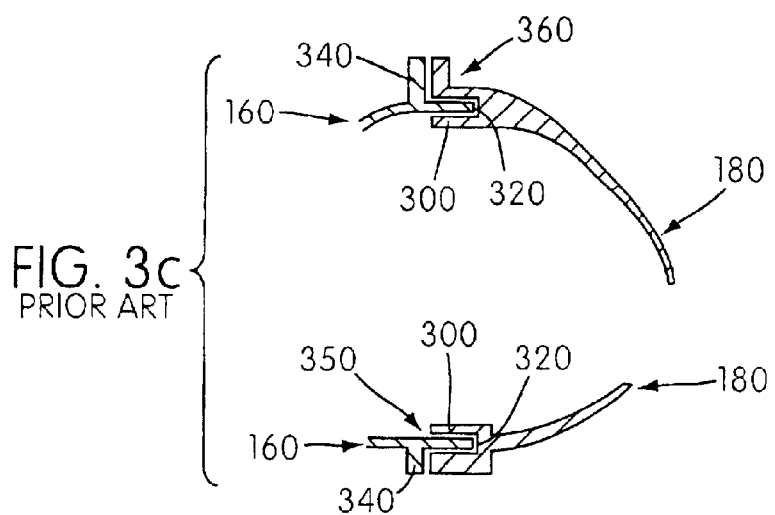
Figure 4A:
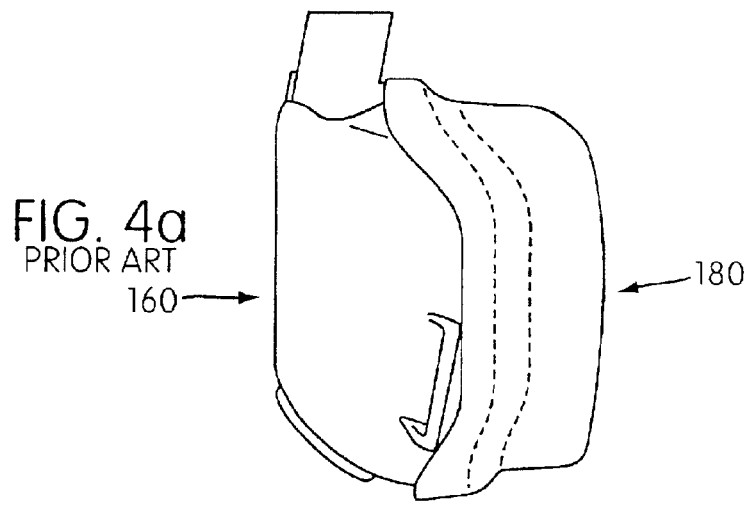
FIG. 4a shows a side view of a prior art mask frame and cushion incorporating a tongue and groove mechanism with a irregular cross-section.
Figure 4B:
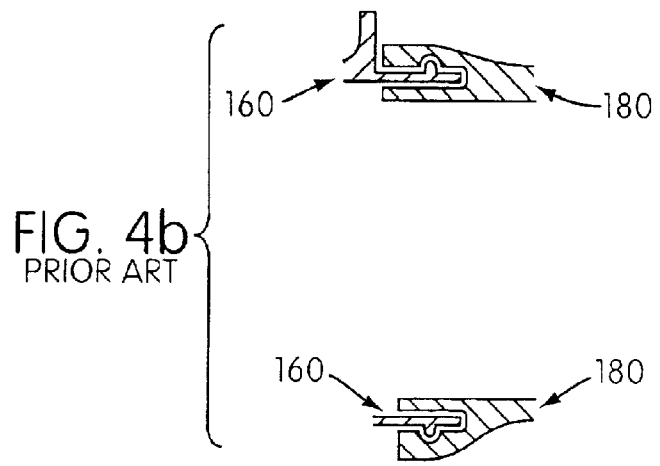
FIG. 4b shows a cross-sectional detail of the mask show in FIG. 4a where the cushion is secured to the frame.
Figure 4C:
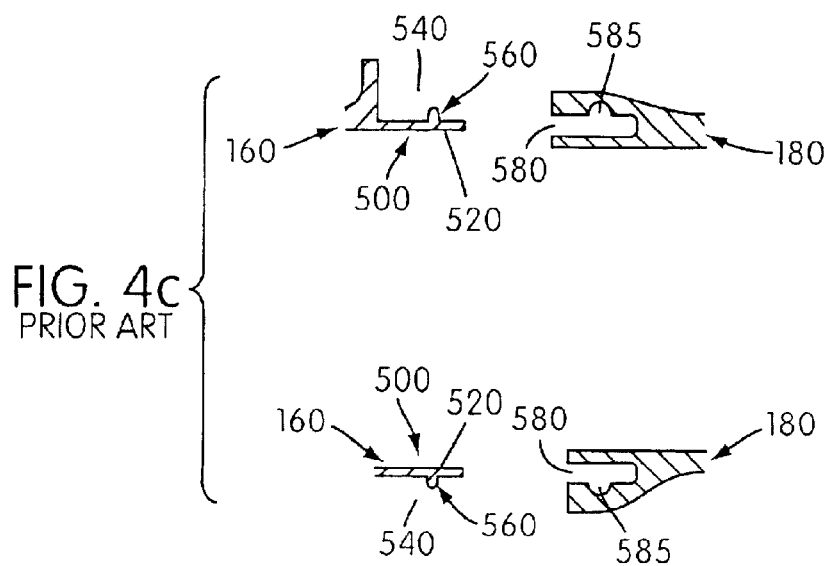
FIG. 4c shows a similar cross-sectional detail of the mask shown in FIG. 4a where the cushion is not secured to the frame.

In an unillustrated embodiment of the invention, the tongue and groove of the frame and cushion have an irregular cross-section, for example as shown in FIG. 4a to 4c.

Although the invention has been described with reference to particular embodiments, it is to be understood that these embodiments are merely illustrative of the application of the principles of the invention. Numerous modifications may be made in the illustrative embodiments of the invention and other arrangements may be devised without departing the spirit and scope of the invention.

What is claimed is:

1. A respiratory mask assembly for delivering breathable gas to a patient, comprising:
   a mask frame defining a cavity with a rear opening, and a rim portion surrounding said rear opening, said rim portion including a laterally extending flange portion and a rearwardly projecting tongue, the flange portion including a rearwardly oriented cushion engagement surface and a forwardly oriented surface including a plurality of recesses angularly spaced about the mask frame;
   a mask cushion to space the mask frame away from the patient's face, said cushion having a rim portion including an end portion to face the cushion engagement surface of the flange portion and a groove in the end portion to receive said projecting tongue of the mask frame, wherein an outer surface of the cushion forms a rearwardly facing shoulder; and
   a clip member over the mask cushion, the clip member having a main body with a first side including a cushion retainer flange that engages a surface behind said shoulder of the cushion, and a second side, opposite the first side, including a plurality of securing tabs each having a surface that engages a respective one of the recesses in the forwardly oriented surface of the flange portion of the mask frame so as to releasably retain the mask cushion on the mask frame, wherein said securing tab includes a resilient detent that is retained forward of said flange portion of the mask frame.

2. A respiratory mask assembly according to claim 1, wherein in said mask assembly is a nasal mask and wherein the collar has three of said tabs.

3. A respiratory mask assembly according to claim 1, wherein in said mask assembly is a full face mask and wherein the collar member has six of said tabs.

4. A respiratory nasal mask assembly for delivering breathable gas to a patient, comprising:
   a substantially rigid nasal mask frame having a generally triangular shape with three sides, the mask frame defining a cavity with a rear opening, and a rim portion surrounding said rear opening, said rim portion including a rearwardly projecting tongue and a laterally projecting flange portion having a rearwardly oriented cushion engagement surface and a forwardly oriented surface having three recesses corresponding to the three sides of the mask frame, the mask frame further including an extension member extending above an apex of the tongue of the mask frame, the extension member including two lateral side walls that define a receiving recess;
   a flexible mask cushion to space the mask frame away from the patient's face, said cushion having a rim portion including an end portion to engage the cushion engagement surface of the mask frame, and a groove in the end portion receiving said tongue of the mask frame, wherein an outer surface of the cushion forms a rearwardly facing shoulder; and
   a selectively engagable and disengagable clip member passing over the mask cushion, the clip member having a main body with a rearwardly oriented side including a cushion retainer flange that engages a surface behind said shoulder of the cushion and a forwardly oriented side consisting essentially of three securing tabs each having a surface that engages with a respective one of the three recesses of the mask frame so as to retain the mask cushion on the mask frame, said clip member including one guide projection positioned at an apex of the clip member opposite one of the three securing tabs, the guide projection having an arcuate portion generally matching a shape the apex of the clip member, wherein
   each of said three securing tabs includes a resilient detent which is retained forward of the flange portion of the frame, and
   the guide projection is positioned in the receiving recess above the apex of the tongue of the mask frame and between the sidewalls of the extension member.

5. A respiratory mask assembly according to claim 4, wherein the mask frame includes an adjustable forehead support coupled to the extension member, the adjustable forehead support including an actuator button configured to be depressed to change the orientation of the adjustable forehead support with respect to the extension member.

6. A respiratory mask assembly according to claim 4, wherein a width of a base of the cushion is about 71.2 mm, a width of a base of an aperture formed in the cushion is about 31.7 mm, and a thickness of the end of the cushion is about 6.6 mm.

7. A respiratory mask assembly according to claim 4, wherein a length of each detent is greater than a width of the guide projection.

8. A respiratory mask assembly according to claim 7, wherein the length is about 18 mm and the width is about 15.5 mm.

9. A respiratory nasal mask assembly for delivering breathable gas to a patient, comprising:
   a substantially rigid nasal mask frame having a generally triangular shape with three sides, the mask frame defining a cavity with a rear opening, and a rim portion surrounding said rear opening, said rim portion including a rearwardly projecting tongue and a laterally projecting flange portion having a rearwardly oriented cushion engagement surface and a forwardly oriented surface consisting essentially of three securing tab recesses corresponding to the three sides of the mask frame, the mask frame further including an extension member extending above an apex of the tongue of the mask frame, the extension member including two lateral side walls that define a guide projection recess positioned opposite to one of the three securing tab recesses; and
   a flexible mask cushion to space the mask frame away from the patient's face, said cushion having a rim portion including an end portion to engage the cushion engagement surface of the mask frame, and a groove in the end portion receiving said tongue of the mask frame, wherein an outer surface of the cushion forms a rearwardly facing clip engagement shoulder.

10. A respiratory mask assembly according to claim 9, wherein the mask frame includes an adjustable forehead support coupled to the extension member, the adjustable forehead support including an actuator button configured to be depressed to change the orientation of the adjustable forehead support with respect to the extension member.

11. A respiratory mask assembly according to claim 9, wherein a width of a base of the cushion is about 71.2 mm, a width of a base of an aperture formed in the cushion is about 31.7 mm, and a thickness of the end of the cushion is about 6.6 mm.

12. A respiratory mask assembly according to claim 9, wherein a length of each said securing tab recess is greater than a width of the guide projection recess.

13. A nasal mask assembly comprising:

a mask frame constructed from a substantially rigid material and including a plurality of recesses;

a mask cushion constructed from a soft material and having a frame-engaging front side including a shoulder portion and a patient-contacting rear side; and a clip adapted to sealingly secure the cushion to the frame, wherein the clip includes a wall portion, a rearwardly located flange portion disposed at a right angle to the wall portion extending in a first direction, the flange being adapted to engage with the shoulder portion of the cushion, and a plurality of resilient detents having a projection adapted to resiliently flex and engage releasably with a corresponding recess of the frame, the projections extending in the first direction.

14. The nasal mask assembly of claim 13, wherein the cushion includes a flange formed on an inner perimeter of the frame-engaging front side which in use is adapted to abut against an inner wall of the frame.

* * * * *